United States Patent [19]

Conner et al.

[11] Patent Number: 4,795,422
[45] Date of Patent: * Jan. 3, 1989

[54] SYSTEM FOR CONTAINMENT AND DIGITAL INSERTION OF SUPPOSITORIES AND OTHER OBJECTS

[75] Inventors: James M. Conner, Old Greenwich, Conn.; Daniel K. Harden, Brooklyn, N.Y.; Donald M. Genaro, Haworth, N.J.

[73] Assignee: Henry Dreyfuss Associates, New York, N.Y.

[*] Notice: The portion of the term of this patent subsequent to Mar. 10, 2004 has been disclaimed.

[21] Appl. No.: 80,908

[22] Filed: Aug. 3, 1987

[51] Int. Cl.4 .................................................. A61F 13/20
[52] U.S. Cl. ........................................... 604/14; 604/54
[58] Field of Search ................................. 604/11–18, 604/289, 904, 54; 206/363, 438, 440

[56] References Cited

U.S. PATENT DOCUMENTS

| | | | |
|---|---|---|---|
| 1,538,679 | 5/1925 | Blinn | 604/59 |
| 2,516,846 | 8/1950 | Betz | 604/59 |
| 2,680,442 | 6/1954 | Linzmayer | 604/59 |
| 2,747,574 | 5/1956 | De Lorenzo | 604/59 |
| 2,754,822 | 7/1956 | Emelock | 604/59 |
| 3,154,074 | 10/1964 | Harrison | 206/364 X |
| 3,358,686 | 12/1967 | Asaka | 604/14 |
| 3,486,504 | 12/1969 | Austin, Jr. | 604/289 |
| 3,753,437 | 8/1973 | Hood | 604/14 |
| 3,857,394 | 12/1974 | Alemany | 604/304 |
| 4,048,998 | 9/1977 | Nigro | 604/14 |
| 4,174,040 | 11/1979 | Wang | 206/529 |
| 4,360,020 | 11/1982 | Hitchcock, Jr. et al. | 604/289 |
| 4,421,504 | 12/1983 | Kline | 604/14 |
| 4,648,867 | 3/1987 | Conner | 604/14 |

FOREIGN PATENT DOCUMENTS

| | | | |
|---|---|---|---|
| 104039 | 3/1984 | European Pat. Off. | 604/12 |
| 2222649 | 12/1972 | Fed. Rep. of Germany . | |
| 2233980 | 1/1975 | France | 604/11 |

Primary Examiner—Samuel Scott
Assistant Examiner—Allen J. Flanigan
Attorney, Agent, or Firm—Fitzpatrick, Cella, Harper & Scinto

[57] ABSTRACT

An improved system for containing and inserting suppositories and objects includes the suppository or object, a sheath which surrounds the suppository or object and is open at one end, a broad-collared ring with an opening therein for passage of the suppository or object and the sheath, and a closure which is removably secured over the opening in the ring.

19 Claims, 2 Drawing Sheets

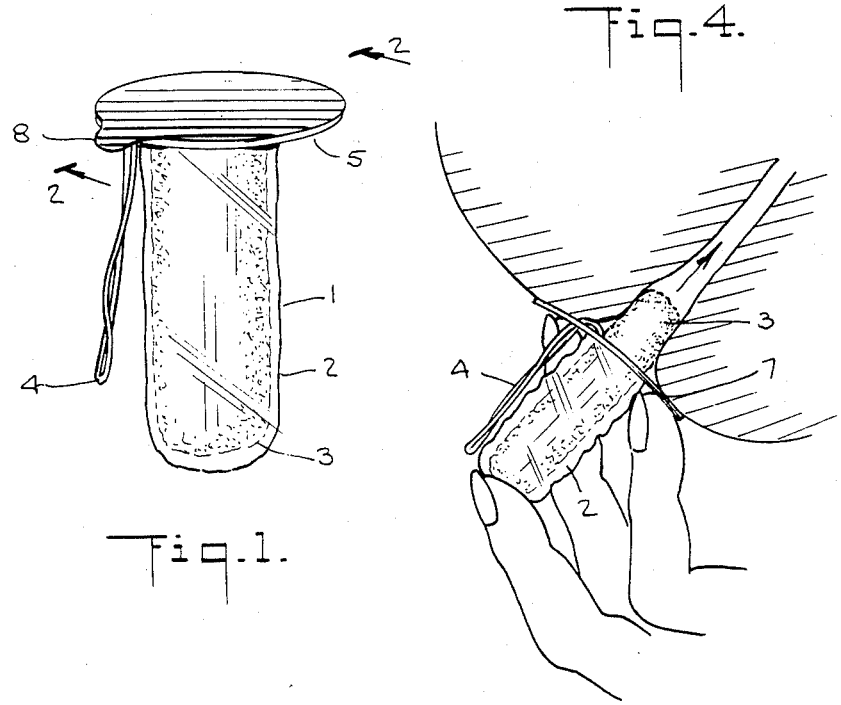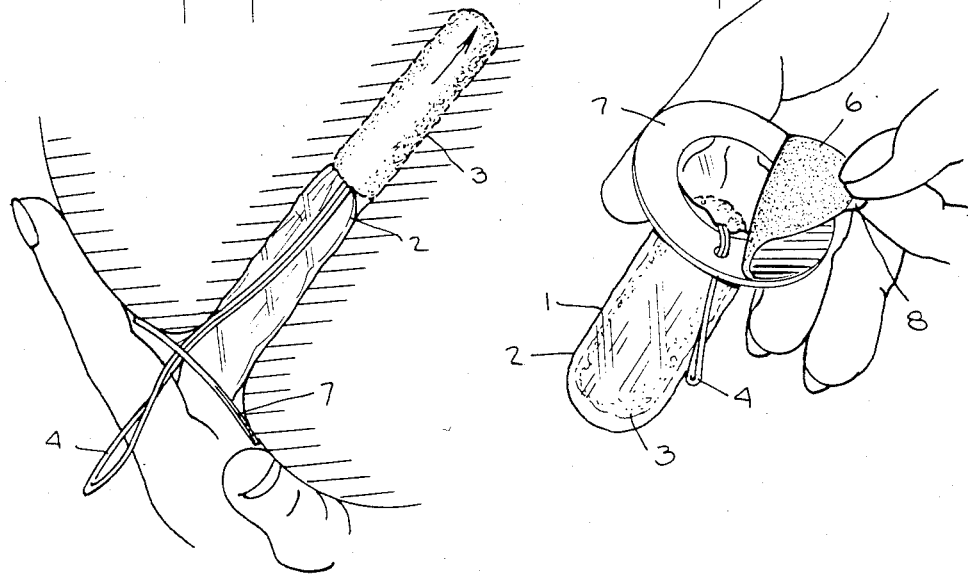

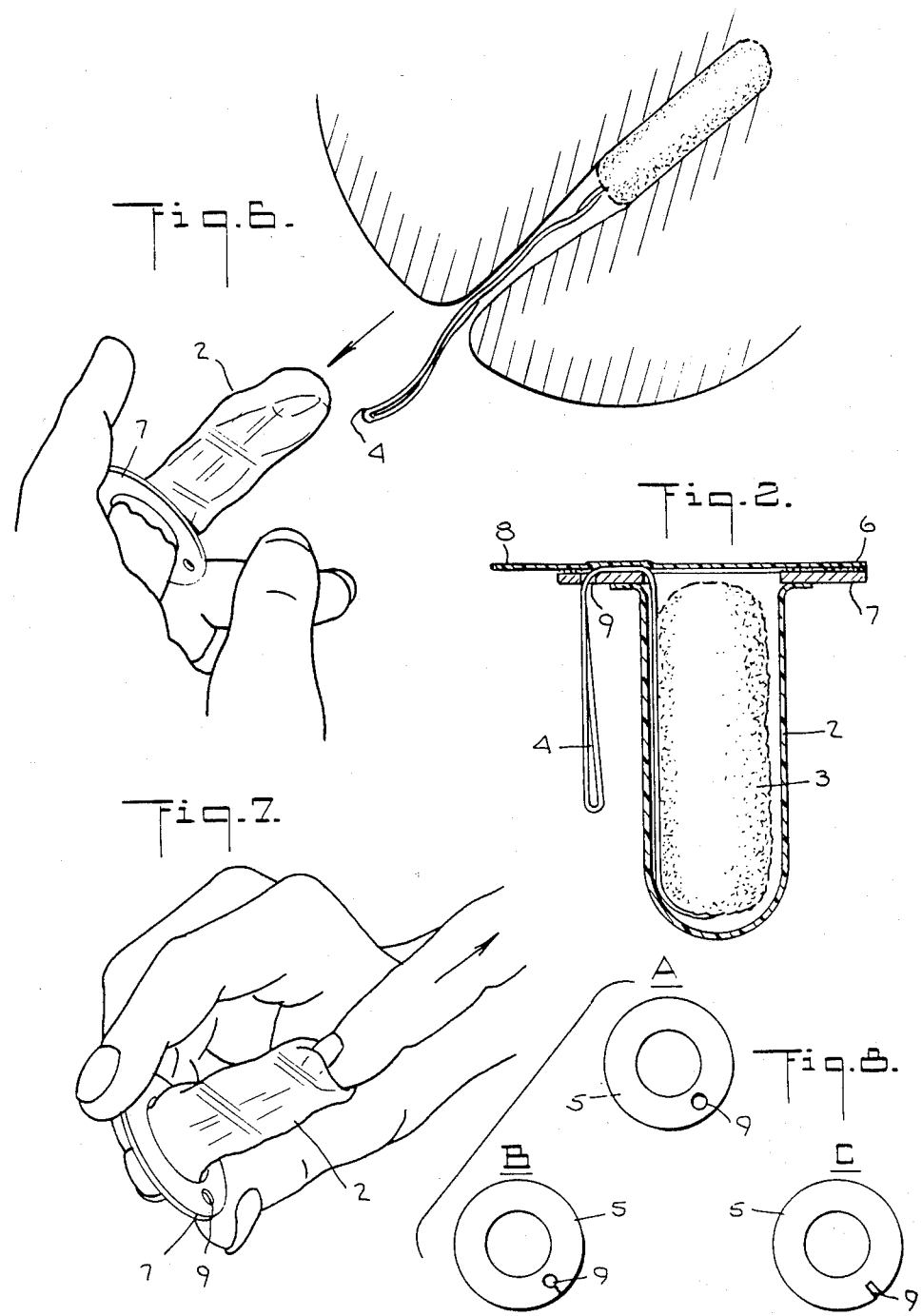

SYSTEM FOR CONTAINMENT AND DIGITAL INSERTION OF SUPPOSITORIES AND OTHER OBJECTS

BACKGROUND OF THE INVENTION

1. Field of the Invention

This invention relates to the containment and administration of suppositories and other objects to be inserted digitally. More specifically, the disclosed device is particularly suitable for sterile containment and sterile insertion of a variety of objects, such as medication, suppositories or tampons, into body openings. In general, the device comprises (i) a package for sanitary storage of an object to be inserted, (ii) a sheath for sanitary digital insertion, and (iii) means for sanitary disposal of the insertion device.

2. Description of the Prior Art

Devices for the insertion of objects are well known and widely used. For example, with respect to suppositories, the most widely accepted method of insertion is by use of insertion devices, although the suppositories may also be inserted by direct placement using one s hand Insertion devices generally include an outer insertion tube, a suppository positioned therein, and a pusher tube, which is placed behind the tampon and within the outer tube These insertion devices are themselves placed into the rectum or other bodily opening and withdrawn along with or subsequent to the insertion of the object.

Insertion by direct placement has the disadvantage of soiling caused by contact between one s hand and the body or bodily opening. While insertion devices may reduce the likelihood or degree of such contact, they constitute a foreign object which some find offensive or uncomfortable inside the body even temporarily. Moreover, prior art insertion devices may not permit the same ease of insertion, location, or comfort as direct insertion because of difficulties in controlling placement of the object. In addition, the insertion device becomes soiled which may make its disposal difficult.

With respect to the insertion of catamenial tampons, a tampon container has been proposed in U.S. Pat. No. 3,358,686, which, if constructed, would comprise a pliable bag to hold the tampon and a semi-rigid plate with four slots therein placed over the open end of the bag. As referred to there, the tampon would be pushed through the pointed flaps in the plate created by the four slots. That container, however, would not provide sanitary protection for the tampon because debris could enter through the slotted openings. Moreover, the sheath and finger could not pass through the slotted openings. The design and location of the pointed flaps created by the slotted openings would be such that, if the bag or a finger were pushed through the slotted openings, the bag or the finger could not be retracted. Upon attempted retraction, the pointed flaps would grip the sheath and finger and tend to prevent their withdrawal.

SUMMARY OF THE INVENTION

The system of this invention provides a sanitary package and permits digital insertion for ease of insertion and precise, comfortable placement with little or no contact between hand and body or body openings and hence with little or no soiling. It also permits sanitary disposal of the used insertion device.

The present invention is particularly suitable for containment and digital insertion of medical suppositories and other objects. In a preferred form, the device provides a sterile receptacle for storage of the object, as well as a device for sterile insertion of the object. Typically, the object to be inserted will be a suppository or a tampon, but it should be understood that a wide variety of objects, such as medication or supply cartridges for machinery, is contemplated The object need not be solid, but may, under the proper conditions, be pellets, granules, gelatin, or even a liquid. Moreover, while the device will normally be used to insert objects into openings in the body, the device may be used in connection with many openings, such as the breech in a dispenser unit or the fuel port for medical irradiation devices.

As contemplated, the present invention comprises three elements in a single assembly: a sanitary package, an object to be inserted, and a sanitary insertion device. The system includes an object to be inserted, a sheath which has an extended cylindrical shape and is closed at one end, a broad-collared ring which has a clear opening therein, add a thin, flat closure which is removably secured over the opening in the ring. The cylindrical sheath surrounds the object to be inserted and has its open end secured to the ring adjacent the opening in the ring such that the sheath may be turned inside-out by passage through the ring and then turned right-side-out to its original position by passage back through that opening. The opening in the ring is sufficiently large and clear that it permits passage of the object as well as passage and withdrawal of the sheath and a finger.

The system of this invention provides several advantages over the prior art. By its combination of sheath and closure, the insertion system of this invention provides a completely sanitary package. For example, devices of this invention may be carried loose in a medical kit or a handbag without danger of contaminating the object to be inserted or the surfaces of the insertion device. The system also permits sanitary, one-handed direct insertion of the object. The broad collared ring provides a shield at the time of insertion, reducing or eliminating contact between hand and body. The opening and sheath permit complete digital insertion while protecting the finger from soiling. After insertion, as the finger is drawn back through the opening in the ring, the sheath may be drawn back through the ring as well, placing the soiled portion inside and making neat disposal possible, particularly if the closure is of a resealable kind and can be returned to its original place after the object has been inserted.

As an additional feature of this invention, a second opening may be provided in the ring through which a withdrawal string attached to the object may be loosely led. This second opening, which is spaced apart from the first opening, may be in the form of a hole, a slit, a slit ending in a hole, or a notch, as desired. By placing the withdrawal string through this opening, during insertion of the object the free end of the string is prevented by friction between the ring and the body from entering the body opening. Upon removal of the ring from adjacent the body, the string is drawn from this opening, leaving it in proper position for later use. In addition, the second opening may be so located that the closure covers and secures it, and the sanitary nature of the package before use is not compromised.

BRIEF DESCRIPTION OF THE DRAWINGS

FIG. 1 is a perspective of a system constructed in accordance with the present invention.

FIG. 2 is a cross-section of FIG. 1 taken at 2—2 in FIG. 1.

FIG. 3 is a perspective of the system of FIG. 1 with the closure partially removed.

FIGS. 4 to 7 are in partial perspective and partial cross-section and show use of the system of FIG. 1.

FIGS. 8A, 8B and 8C show variations of the broad-collared ring of this invention.

DESCRIPTION OF THE PREFERRED EMBODIMENT

The invention will be described with specific reference to a system for containing and storing suppositories. However, as described above in the Summary, the invention is adaptable to the insertion of a wide variety of objects into different types of openings, and therefore should not be limited to the particular embodiment disclosed herein.

Referring now specifically to the drawings, reference numeral 1 identifies a suppository system of the present invention, which includes a protective sheath 2 (semi-transparent in these drawings but which may preferably be opaque), a suppository 3, and a withdrawal string 4. Reference numeral 5 refers to the combination of the broad-collared ring 7 and the removable closure 6 with its tab 8. As shown in FIGS. 2 and 3, the withdrawal string 4 passes through second opening 9.

FIG. 3 shows the removal of the closure 6 by pulling on its tab 8 to peel it off of broad collared ring 7. As shown in FIGS. 4 and 5, during insertion the ring can reduce or eliminate contact between the outside of the body and the hand. In FIG. 5, the suppository is fully inserted, and the sheath and finger have passed fully through the clear opening in the broad-collared ring 7. Tactile feed back eases adjustment and optimum placement. The withdrawal string 4 is now outside the sheath and in its proper location held by the ring 7 in its opening 9. The broad-collared ring, by providing a stop, facilitates one-handed insertion.

As is apparent, the surface of the sheath which was originally on the exterior has made no contact with the body orifice. Only the previously interior and sanitary surface has made such contact. In addition, the inserting finger has made no contact with the body orifice.

In FIG. 6, the suppository is shown in place, with the sheath and ring removed from the body. Figure 7 shows the finger being removed from the suppository insertion device, which is being returned to its original orientation with respect to the ring, thus placing the soiled surface inside.

The suppository may be any of various well-known medicated suppositories having a cylindrical or conical shape, although the invention is not limited to the insertion of objects having only these shapes. The sheath may be made of latex, treated paper or other synthetic or natural flexible, thin material. The broad-collared ring may be made of cardboard or other flat, thin, rigid or semi-rigid material, with the sheath adhered by adhesive onto the collar or held between two laminated pieces which may be used to make up the broad-collared ring. The closure may be made of paper, foil, or other similar material, and is removably secured to the ring by use of a peelable adhesive or other securing means. Alternatively, the closure and the ring may be cut from the same piece of material in a dumb-bell shape, with the closure folded over to cover the opening in the ring. If the closure is made of a properly selected material, such as a foil, the package can be made tamper-proof. All parts of the suppository system are preferably biodegradable.

Exemplary dimensions of the system for the ring are an overall diameter of one and one-half inches, with an opening seven-eighths of an inch in diameter, a suppository length of about two inches, and a sheath of about 2½ inches in length and seven-eighths of an inch in diameter.

The foregoing is considered illustrative of the principles of the invention. Variations and modifications will be recognized, and it is hence not desired or intended to limit the invention to the exact construction and procedures described. Rather, all appropriate modifications and equivalents may be used.

We claim:

1. A containment and digital insertion system comprising:

an object to be inserted into an opening;

an impermeable sheath which surrounds the object and is open at one end, said sheath being unattached to said object; and a broad-collared ring which has an unobstructed opening therein for passage and withdrawal of a finger and the sheath and to which the open end of the sheath is affixed such that the opening in the sheath registers with the opening in the ring, the above elements being arranged such that (a) the portion of the sheath which contacts the opening is shielded from external conditions, (b) the object, the sheath, and a finger can pass through the opening for digital insertion and location of the object, (c) while inserting the object, the finger is protected by the impermeable sheath from soiling, and (d) the sheath can be retracted through the opening to provide for clean disposal of the used sheath.

2. The system of claim 1, wherein said object comprises a suppository.

3. The system of claim 1 in which the object includes a withdrawal string and the ring includes a second opening spaced apart from the opening in the ring, said string being led from the object out of the sheath through the opening in the ring and then back in the opposite direction through the second opening.

4. The system of claim 1 further comprising a sanitary sealing closure removably secured over the opening in the ring.

5. The system of claim 4 in which the closure is peelable.

6. The system of claim 5 in which the closure is resealable.

7. The system of claim 4 in which the sheath, the ring and the closure in combination constitute a sanitary package for the object and provide sanitary protection to the portion of the sheath which contacts the interior of the opening.

8. The system of claim 1 in which the sheath, the ring and the closure in combination constitute a sanitary, impermeable package for the object.

9. The system of claim 7 in which the closure is planar, impermeable, and arranged such that before removal it provides sanitary protection to the object.

10. The system of claim 9 in which the opening in the ring remains unobstructed without application of radial pressure on the ring.

11. The system of claim 1 in which the broad-collared ring is flat.

12. The device of claim 7 in which the broad-collared ring is flat, thin, and sufficiently rigid to maintain an unobstructed opening without application of force.

13. A device for sanitary packaging and insertion of an object, comprising:
   a sheath which is open at one end, said sheath being unattached to said object;
   a broad-collared ring with an unobstructed opening therein to which the sheath is affixed in a location such that the sheath and object can pass through the opening therein and the sheath can then be retracted back through said opening; and a sealing closure which is secured over the opening in the ring.

14. The device of claim 13, wherein said object comprises a suppository.

15. A device for sanitary packaging and insertion of an object, comprising:
   a sheath which is open at one end;
   a broad-collared ring with an unobstructed opening therein to which the sheath is secured in a location such that the sheath can pass through the opening therein and then be retracted back through said opening; and a closure which is secured over the opening in the ring;
   in which device the ring includes second opening spaced apart from the first opening.

16. The device of claim 15, wherein said object comprises a suppository.

17. A method of inserting an object comprising the steps of:
   placing the object inside an impermeable sheath which is capable of surrounding the object, is not attached to the object, and is open at one end;
   affixing at the open end of the sheath a broad-collared ring which has an unobstructed opening therein that permits unobstructed passage and withdrawal of a finger and the sheath to its original position;
   removably securing a sealing closure over the opening in the ring;
   removing the removable closure;
   placing the broad-collared ring adjacent an opening;
   inserting the object into the opening by means of digital pressure on the sheath and passage of a finger free from soiling and the sheath through the opening in the broad-collared ring;
   contacting the opening only with sanitary portions of the sheath;
   withdrawing the sheath from the opening; and
   removing the finger from the broad-collared ring.

18. The method of claim 17 including the additional step of returning the sheath to its original position.

19. The method of claim 17 including the step of selecting a closure which is planar and impermeable, and arranging said closure such that before removal it provides sanitary protection to the object.

* * * * *

UNITED STATES PATENT AND TRADEMARK OFFICE
CERTIFICATE OF CORRECTION

PATENT NO. : 4,795,422

DATED : January 3, 1989

INVENTOR(S) : James M. Conner, et al.

It is certified that error appears in the above-identified patent and that said Letters Patent is hereby corrected as shown below:

COLUMN 1
       Line 23, "one s" should read --one's--.
       Line 24, "hand" should read --hand.--.
       Line 27, "tube" should read --tube.--.
       Line 32, "one s" should read --one's--.

COLUMN 2
       Line 23, "add" should read --and--.

COLUMN 3
       Line 42, "ing 9" should read --ing 9.--.

COLUMN 4
       Line 5, "tamper-proof" should read --tamperproof--.
       line 66, "claim 7" should read --claim 4--.

COLUMN 6
       Line 1, "second opening" should read --a second opening--.

Signed and Sealed this

Sixth Day of February, 1990

*Attest:*

JEFFREY M. SAMUELS

*Attesting Officer*    *Acting Commissioner of Patents and Trademarks*